(12) United States Patent
Westermarck et al.

(10) Patent No.: US 6,203,835 B1
(45) Date of Patent: Mar. 20, 2001

(54) USE OF HYDROXY ACID OR A PRODUCT CONTAINING THE SAME IN ANIMAL FEED

(75) Inventors: Hakon Westermarck, deceased, late of Helsingfors, by Alma Ingrid Westermarck, Eva Marina Finckenberg, Joel Christer Westermarck; Tuomas Walter Westermarck; by Jan Mikael Westermarck, heirs, both of Esbo; Juha Apajalahti; Pentti Hietala, both of Helsinki, all of (FI); Maire Jaarma, Hägersten (SE)

(73) Assignee: Oy Extracta Ltd., Helsinki (FI)

( * ) Notice: Subject to any disclaimer, the term of this patent is extended or adjusted under 35 U.S.C. 154(b) by 0 days.

(21) Appl. No.: 08/981,108

(22) PCT Filed: Jun. 20, 1996

(86) PCT No.: PCT/FI96/00364

§ 371 Date: Dec. 28, 1998

§ 102(e) Date: Dec. 28, 1998

(87) PCT Pub. No.: WO97/00621

PCT Pub. Date: Jan. 9, 1997

(30) Foreign Application Priority Data

Jun. 21, 1995 (FI) .......................................... 953090
Jun. 20, 1996 (FI) .......................................... 962603

(51) Int. Cl.$^7$ ................................. A23K 1/00; C12P 7/56
(52) U.S. Cl. ............................. 426/335; 426/53; 426/321; 426/807
(58) Field of Search .................................. 426/335, 807, 426/321, 53

(56) References Cited

U.S. PATENT DOCUMENTS

| | | | |
|---|---|---|---|
| 3,761,518 | * 9/1973 | Haglid | 260/535 R |
| 4,160,041 | * 7/1979 | Schroeder et al. | 426/69 |
| 4,175,121 | * 11/1979 | Mantha | 424/94 |
| 4,363,815 | 12/1982 | Yu et al. | 424/274 |
| 4,380,549 | 4/1983 | Van Scott et al. | 424/317 |
| 4,388,327 | * 6/1983 | Cummins | 426/2 |
| 4,617,155 | * 10/1986 | Tanaka et al. | 260/501.12 |
| 4,670,269 | * 6/1987 | Abdel-Monem | 426/74 |
| 4,772,592 | 9/1988 | Benzoni | 514/63 |
| 4,956,188 | * 9/1990 | Anderson | 426/74 |
| 5,028,440 | * 7/1991 | Nissen | 426/2 |
| 5,389,679 | 2/1995 | Alliger | 514/557 |
| 5,459,053 | 10/1995 | Rasmussen | 435/139 |

FOREIGN PATENT DOCUMENTS

| | | |
|---|---|---|
| 1080667 | * 8/1967 | (GB). |
| 50014625 | * 2/1975 | (JP). |
| WO 91/11111 | 8/1991 | (WO). |

OTHER PUBLICATIONS

Featherston et al., Poultry Sci., vol. 53(2), pp 680–686, 1974.*
Monsanto, Chemical & Engineering News, Apr. 15, 1991.*
Feedstuffs, pp. 13, Nov. 11, 1991.*
The Merck Index, Eleventh Edition, p. 943 Published by Merck & Co, Inc., New Jersey, USA, 1989.*
Morrison et al., "Diazonium Salts, Preparation and Reactions", Organic Chemistry, 5th Edition, pp 973–975.
Hietala et al., Nutr. Metab. 23:227–234 (1979), with computer generated Abstract.
Merck Index, "D–Lactic Acid", p. 842, Eleventh Edition.

* cited by examiner

*Primary Examiner*—C. Sayala
(74) *Attorney, Agent, or Firm*—Armstrong, Westerman, Hattori, McLeland & Naughton

(57) ABSTRACT

The present invention relates to a hydroxy acid or a product containing thereof and a product made containing the same. The invention is characterized by the use of the hydroxy acid as a feed additive, either alone or in combination with other useful compounds or a product containing the same.

11 Claims, 10 Drawing Sheets

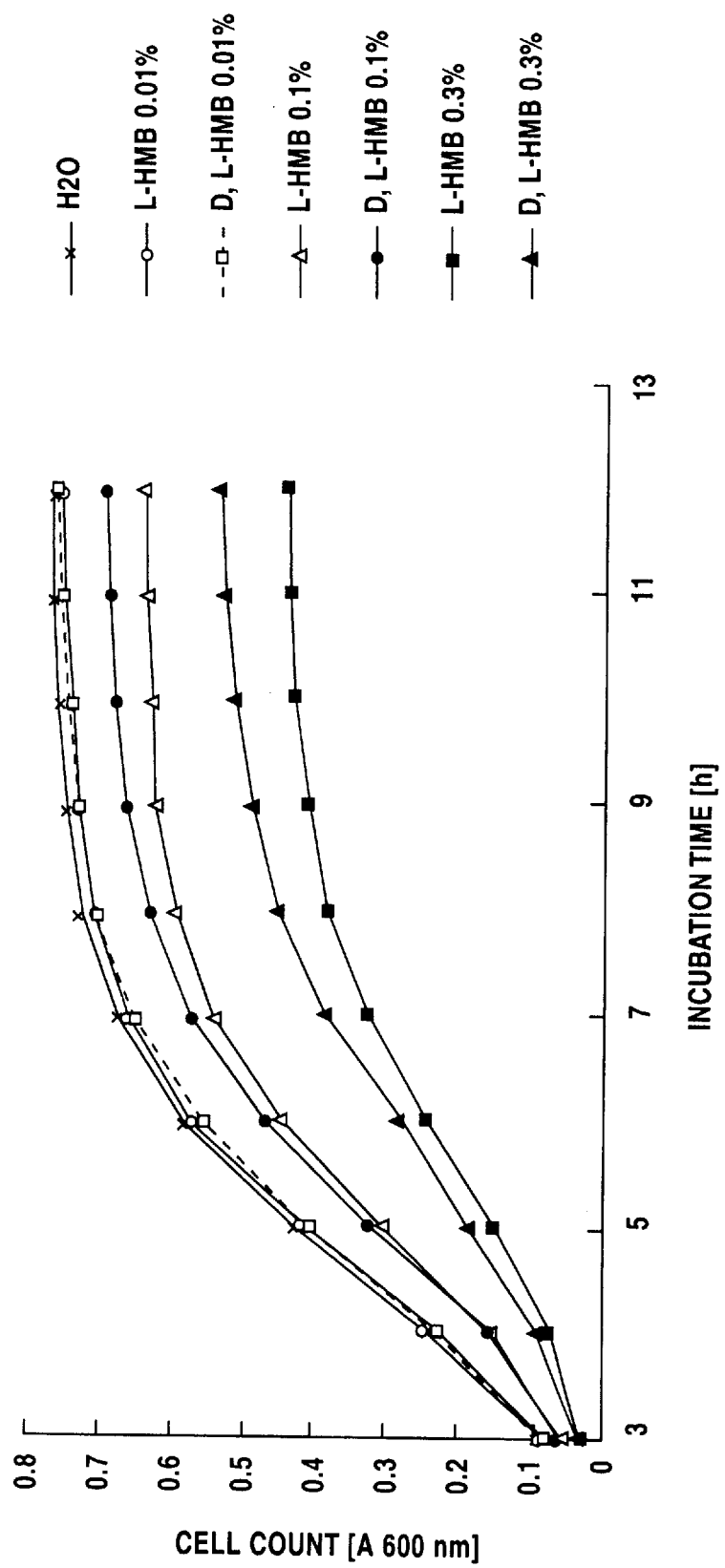

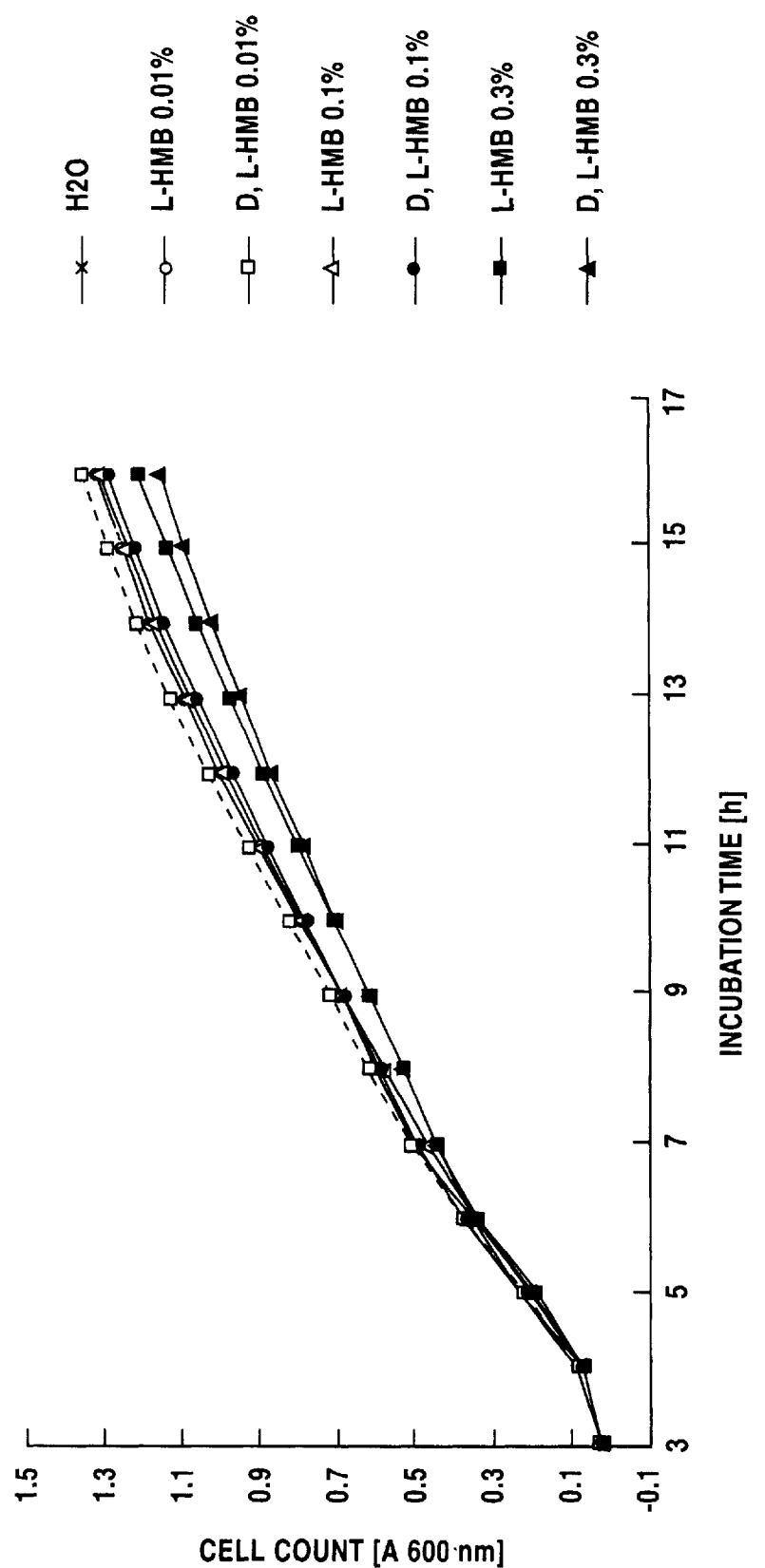

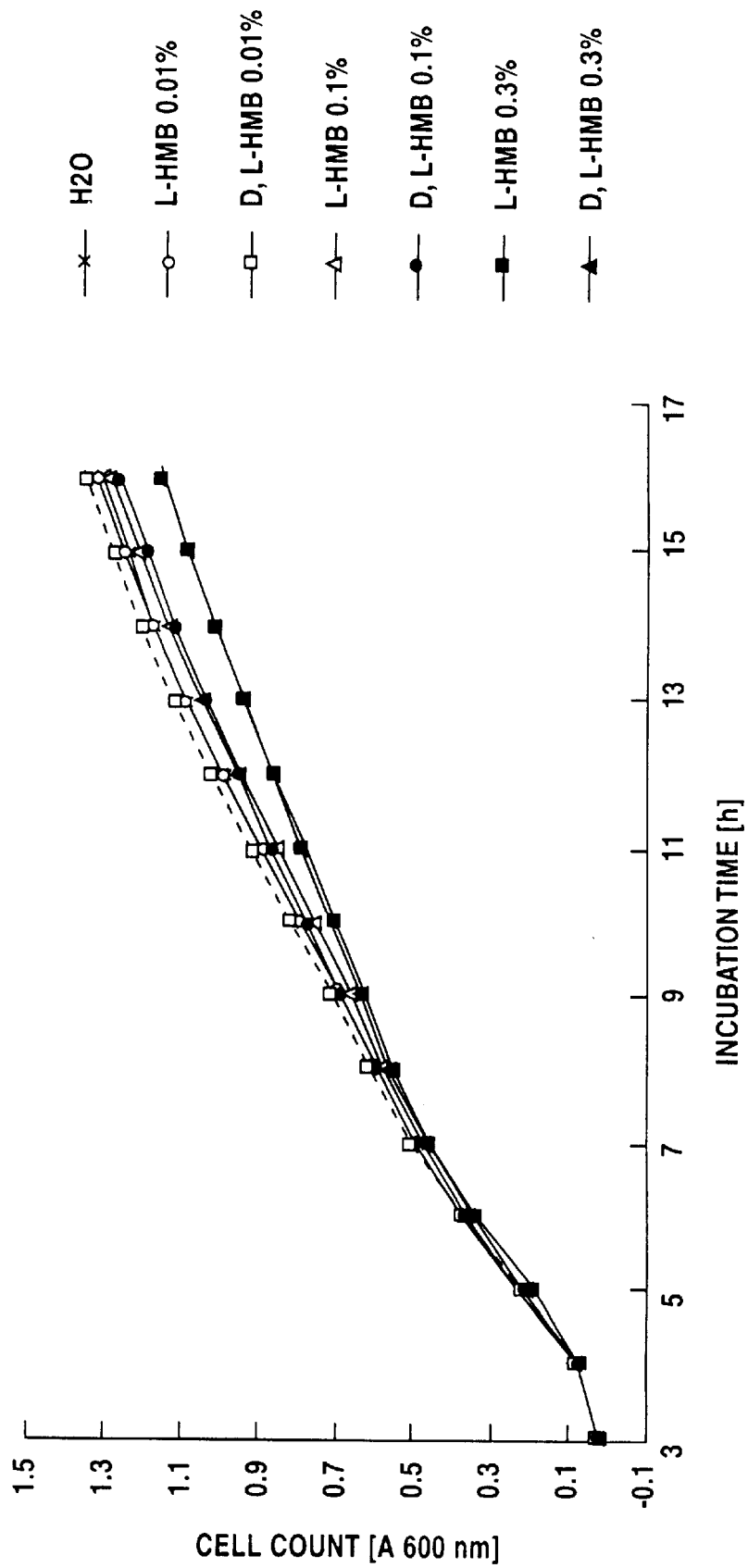

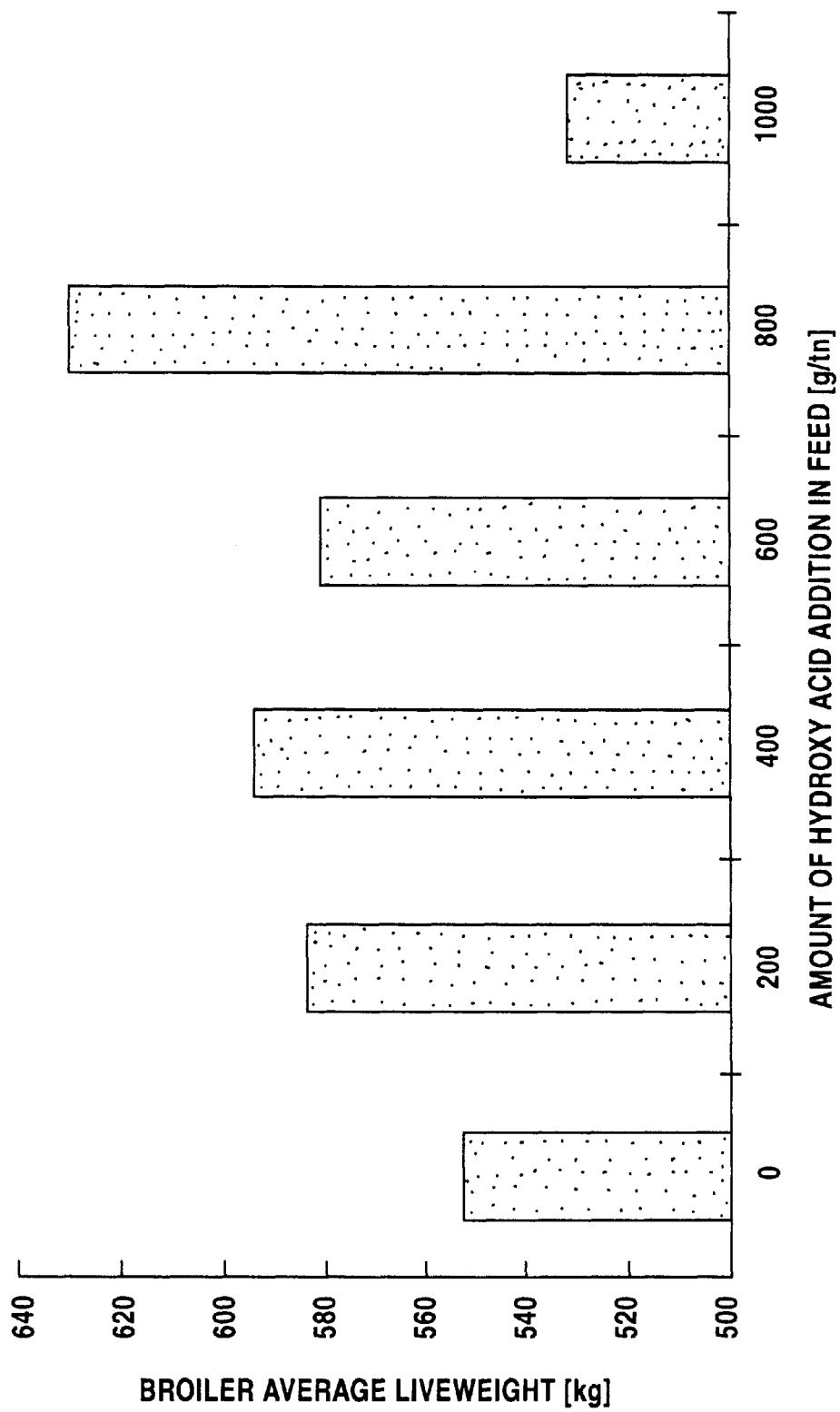

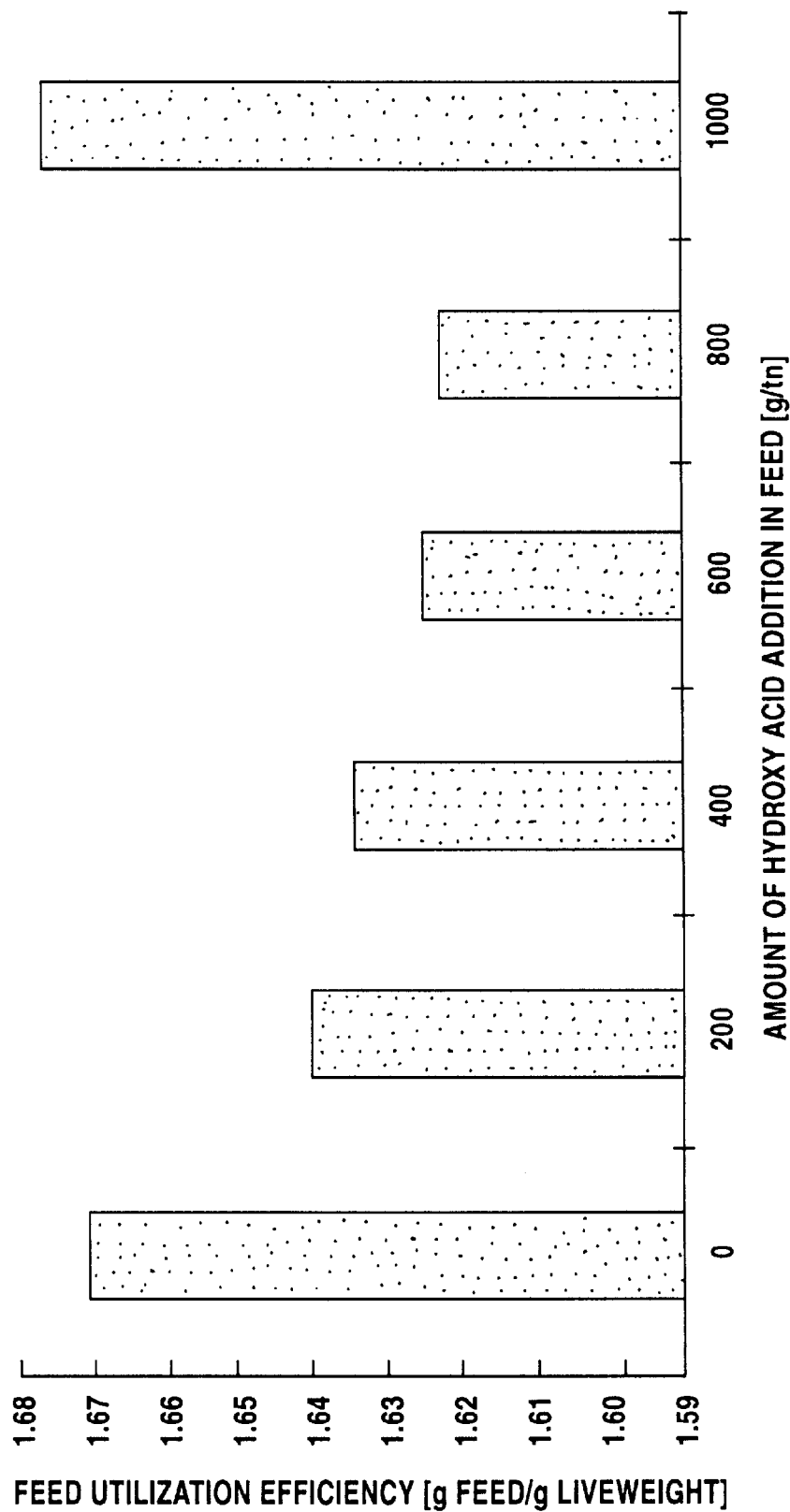

USE OF HYDROXY ACID OR A PRODUCT CONTAINING THE SAME IN ANIMAL FEED

The present invention relates to the use of a hydroxy acid or a product containing the same and a product made thereof.

Bacteria of the genus Salmonella are well known pathogenic organisms which are much feared when occurring in animal feed and foodstuffs of animal origin. A primary infection caused by Salmonella arises when the bacterium starts to multiply in the alimentary tract of animals and therefrom is capable of contaminating both the host body and the end products (eggs, milk) products by the animal and conventionally used as nutrients. If allowed to pass uncontrolled to distribution, such contaminated foodstuffs can cause serious health hazards and economic losses in the population. Besides pathogenic microbes such as Salmonella strains, enteropathogenic *Escherichia coli* strains and campylobacteria, the food production efficiency of animals is also negatively affected by a plurality of microbes normally present in the alimentary tract flora of animals when occurring in excessive amounts. These microbes utilize the nutrients contained in the feed in the same fashion as the host animal, thus competing with their host for the feed. To suppress these microbes, so-called growth-promoting antibiotics are conventionally added in the feeds. Microbes often isolated from the small intestine can be grossly categorized in three groups: coliforms, enterococci and lactic acid producing bacteria. The latter group species are claimed to have positive effects on animal health though the actual mechanisms involved are not known accurately.

The use of lactic acid producing bacteria for processing and preserving different material has been long known. In addition to silage processing, lactobacilli are utilized in the manufacture of, e.g., a variety of dairy products. As known from long-term practical experience of every-day use, such fermented diary products in particular have advantageous health-promoting properties. Today, products containing lactobacilli are also available for the normalization of the bacterial flora in the alimentary tract when the microbial flora has changed due to, e.g., a treatment with an antibiotic drug. Typically, lactobacilli form an essential component in the microbial flora of the alimentary tract. The metabolic products of these commensal bacteria are considered to have a great importance to the welfare of animals and man.

It is an object of the present invention to provide a novel use for hydroxy acids as antimicrobial components in animal feeds. It is a further object of the invention to provide a feed improver based on hydroxy acids. It is still a further object of the invention to achieve a method of producing and using such feed improvers containing hydroxy acids.

The invention offers significant benefits.

An important species in the genus of lactobacilli is *Lactobacillus plantarum*. This bacterium species is present in a plurality of different media. *L. plantarum* is a so-called homofermentative lactic acid producing species. Accordingly, fermentation by this species produces almost purely lactic acid with small amounts of acetic acid and ethanol. *L. plantarum* can by virtue of the present invention now be persuaded to use protein-containing animal and plant waste, whereby the fermentation forms beside lactic acid, also relatively high amounts of other hydroxy acids. Here, the invention makes it possible to utilize hydroxy acids particularly as a feed improver. The characterizing properties of the invention are disclosed in the annexed claims. Since hydroxy acids have a microbicidal effect, they can give the product a very long storage time as a feed. Simultaneously, any microorganisms pathogenic to animals or man contained in the raw materials are destroyed entirely.

The hydroxy acids, or mixtures thereof, utilized in accordance with the invention can be either synthesized chemically or produced biotechnically into, e.g., a fermentation solution containing the bacterium. An essential requirement herein is that the acid contains most preferably at least 4 carbon atoms and/or having a branched carbon chain or an aromatic or other suitable substituent. Particularly advantageous in this aspect are 2-hydroxy-3-methyl butyric acid, 2-hydroxy-4-methyl valeric acid or a mixture thereof.

Furthermore, the invention concerns a feed improver which contains a hydroxy acid in an amount which is effective either alone or in combination with other compounds. According to the invention, the feed improver is either added in the feed or produced therein. A feed improver is defined as a component added in the feed typically at a level of 0.01–1%, with its function being to improve the health, growth other productivity factor of an animal. The effect of the feed improver may be directed on the microbial flora, digestive enzymes, resorption of nutrients in the alimentary tract, metabolic processes of the host animal or some another selected object. Depending on the object animal, the feeds concerned are typically comprised of a cereal or other similar starch-containing component (wheat, oats, rye, corn, etc.), a protein source (soya, turnip rape, fish meal, etc.), a fat source (vegetable oil or animal fat), mineral salts, amino acid supplements if the protein source is unbalanced, and vitamins as well as trace elements. A feed ration for ruminants contains a substantial amount of fiber-rich forage (silage, grass, etc.) and less starch. According to examples to be described later, broiler chickens require about 400–1600 mg of hydroxy acid during their life (approx. 40 days). This amount corresponds to about 200–800 g of hydroxy acid per tn of feed. Other animals such as pigs and egg-laying hens received in said examples about 20–100 mg hydroxy acids per kg liveweight a day. According to the invention, the daily administration of hydroxy acid is less than 500 mg hydroxy acids per kg liveweight a day, advantageously 20–100 mg hydroxy acids per kg liveweight a day. Hydroxy acids were found to affect microbial growth in vitro already at a level less than 0.1% (1000 g/tn feed). Hence, the amount of hydroxy acids in feed is advantageously 0.01–1%, most advantageously not more than 0.1%.

The adapted *L. plantarum* strain forms significant amounts of alpha-hydroxy acids, the hydroxy acid concentration in fermentation media being about 2%. In addition to d,l-lactic acid, the most important acids formed are d,l-2-hydroxy-3-methyl butyric acid and d,l-2-hydroxy-4-methyl valeric acid. The formation according to the invention of d,l-2-hydroxy-3-methyl butyric acid and d,l-2-hydroxy-4-methyl valeric acid in the fermentation media of *L. plantarum* has not been disclosed earlier nor the effect of these compounds on the growth of microbes has been investigated. In the recovery of d,l-2-hydroxy-3-methyl butyric acid and d,l-2-hydroxy-4-methyl valeric acid from the fermentation media, *Escherichia coli* was used as the test organism for determining the distribution of the antimicrobial effect in the different fractions. Particularly unexpected is that these acids have an antimicrobial effect on a very large selection of different types of microorganisms. As can be noted from Example 5 later, these compounds have been shown to exhibit an antimicrobial effect on about seventy different micro-organisms. Further unexpected is that the alpha-hydroxy acids concerned in the invention are compounds which are considered to be normally occurring metabolites in animal organisms. On this basis, it initially seemed plausible that at least some organisms could in their metabolic pathways transform these compounds, thus inactivating them.

The fermentation is carried out in vessels of 2–10000 liter volume. The milled medium, which is preferably steamed to destroy an vegetative microbial cells contaminating the raw material consisting of fish cleaning waste, blood, leguminous material or abattoir waste is seeded with a suitable amount of cultivated seed suspension of *L. plantarum*, the medium is mixed and the fermentation is allowed to continue for 6–7 days. The temperature of the suspended medium rises to about +30° C. At the end of the fermentation, the suspension pH is 3.8–4.0. During the fermentation, the initially thick pulped mass changes into a move fluid form, whereby it can be easily discharged into drums used as storage/transport containers. During extended storage of the fermentation product, the oil or fat contained in the solution forms a supernatant floating on the surface of the solution, whereby it by most can be skimmed off from above the solution. This possibility is particularly important when the raw material consists of a mixture of small fish and fish cleaning waste, because fish oil is rich with polyunsaturated fatty acids, particularly EPA and DHA.

The acids isolated from the fermentation media principally comprise d,l-2-hydroxy-3-methyl butyric acid and d,l-2-hydroxy-4-methyl valeric acid. Comparison of the microbial growth inhibiting effect of pure synthetic acids with the anti-microbial effect of the fermentation medium indicated that said acids in combination with the d,l-lactic acid formed into the medium stand for the entire non-volatile and nonvanishing antimicrobial efficiency of the fermentation solution.

Pure forms of the above-mentioned alpha-hydroxy acids can be made using a variety of conventional methods. One of such methods comprises deaminating an amino acid or a mixture of amino acids with nitrite into corresponding alpha-hydroxy acids, extracting the latter into an organic solvent and evaporating the solution thus obtained, whereby the end product remaining is a mixture of alpha-hydroxy acids. Now these conventional methods are surpassed by the method according to the invention which offers a new way of preparing alpha-hydroxy acids in a fermentation medium.

The acting mechanism of alpha-hydroxy acids on microbes is unclear. It is plausible that these acids act as antimetabolites of the corresponding alpha-amino acids. It must be noted that, e.g., 2-hydroxy-4-methyl valeric acid is a competitive inhibitor of leucine amino peptidase. The acidities of the d,l-2-hydroxy-3-methyl butyric acid and the d,l-2-hydroxy-4-methyl valeric acid are identical: both have a $pK_a$=3.80. Hence, the mixture of the acid and a salt of said acid with a strong base exhibits a maximum buffer capacity at pH 3.8, which is of particular importance in treating, e.g., microbial infection and inflammation conditions of the skin and the oral cavity. According to present understanding, these compounds have no active resorption mechanism in the gastrointestinal tract, but rather, their resorption occurs via passive diffusion. Therefore, their retention in the alimentary tract is longer than that of, e.g., lactic acid. After their resorption into the organism, these acids are metabolized through the same paths as the corresponding alpha-amino acids. As their catabolism in the animal organism is complete, no residues from, e.g., animal-waste-based feed will remain in the products. However, their catabolic disintegration rate in the organism may be relatively slow, because the lactic dehydrogenase enzyme produced by an animal organism is incapable of oxidizing such alpha-hydroxy acids whose structure contains a branched carbon chain into corresponding keto acids, as in the case with d,l-2-hydroxy-3-methyl butyric acid and d,l-2-hydroxy-4-methyl valeric acid. When administered intravenously to mice, the $LD_{50}$ values of the sodium salts of these acids are:

Na-salt of d,l-2-hydroxy-3-methyl 1080 mg/kg

Na-salt of d,l-2-hydroxy-4-methyl 650 mg/kg

In the following, the invention will be described in greater detail with the help of the following examples and with reference to annexed drawings in which

BRIEF DESCRIPTION OF DRAWINGS

FIGS. 3*a* and 3*b* are plots of the efficacy of HMV and HMB, respectively, in inhibiting the growth of an Enterococcus bacterium strain (111) isolated from the broiler chicken gastrointestinal tract;

FIGS. 4*a* and 4*b* are plots of the efficacy of HMV and HMB, respectively, in inhibiting the growth of a lactic acid bacterium strain (120) isolated from the broiler chicken gastrointestinal tract;

FIG. 5 is plot of the average weight of broilers in the different test animal groups after three weeks feeding;

FIG. 6 is plot of the effect of the hydroxy acids on the efficiency of feed utilization in test animal groups after three weeks feeding.

DETAILED DESCRIPTION

Figure 1A:
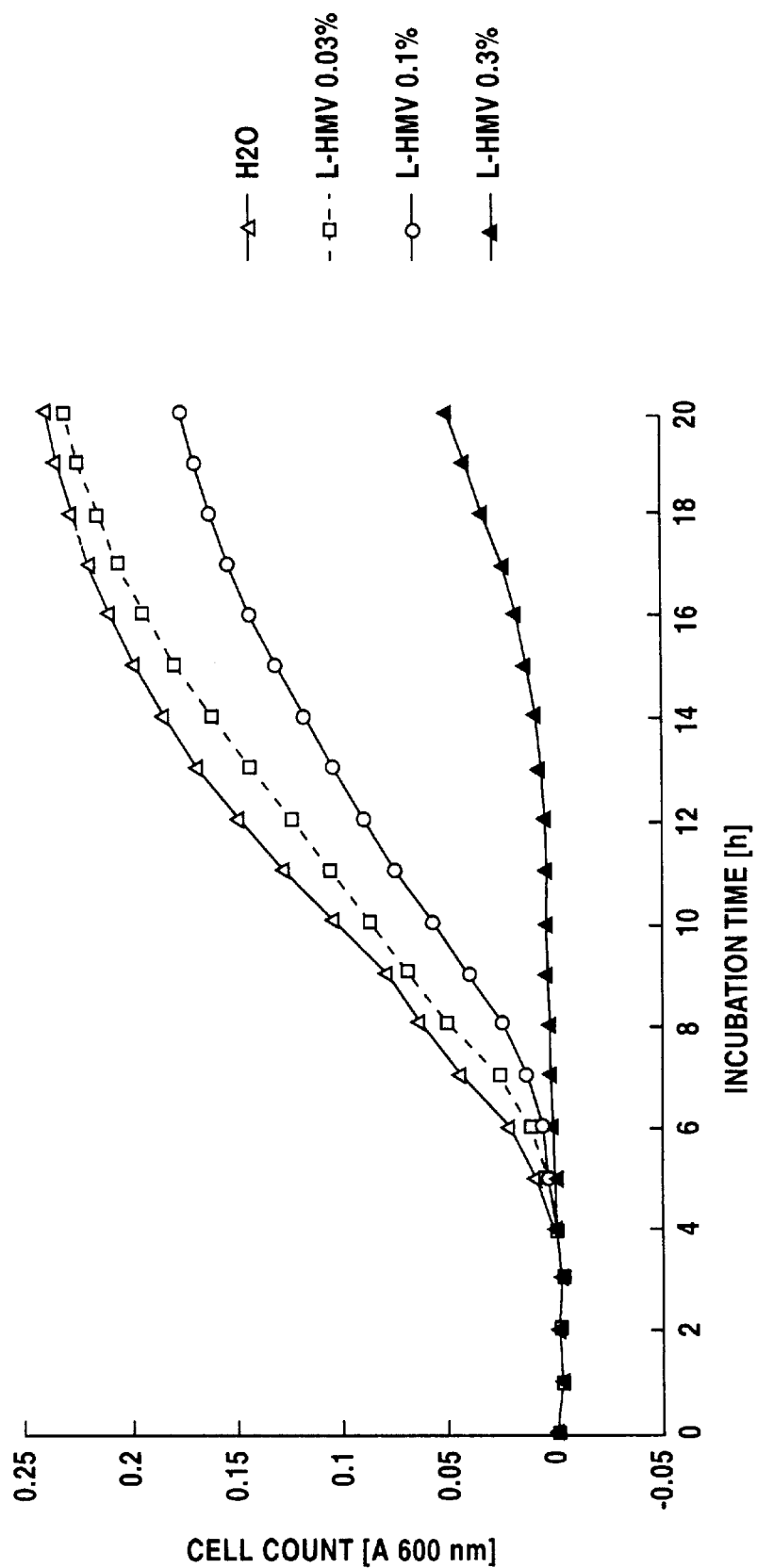
FIGS. 1*a* and 1*b* are plots of growth inhibition of *E. coli* and *S. aureus* by HMV (L-2-hydroxy-4-methyl valeric acid) and HMB (L-2-hydroxy-3-methyl butyric acid), respectively.

The examples illustrate the method of adapting *L. plantarum* to produce alpha-hydroxy acids, the effect of these acids on micro-organisms and the processes used in preparation of solutions containing these acids.

EXAMPLE 1

This test was carried out to test the adaptation of *L. plantarum*.

Lyophilized *L. plantarum* strains were obtained from a culture provided by Chemical Research Laboratory, Teddington, Middlesex, England. Litmus milk was used as the normal culture medium for *L. plantarum*. The normal growth optimum of the strain is +28–+30° C. The adaptation of the strains was made by lowering the temperature +22–+24° C. Then, the growth was at a much slower rate than at the higher temperature. Next, boiled fish broth was added in the fermentation medium, in which litmus milk was the main consistent, starting from 1 vol.-% and by continuous addition/stirring gradually increasing the proportion of the fish broth to 10 vol.-% in the fermentation medium.

Preparation of boiled fish broth: 2 kg of raw Baltic herring was cleaned (leaving the spine). About 700 g of cleaned herring is obtained from a 1000 g raw weight of uncleaned herring. The cleaned herring was chopped into pieces and boiled in one liter volume of water for 30 min under a tight cover. The boiled broth was twice filtered through a sieve cloth and sterilized.

The culture thus adapted was used to seed a growth medium containing rye bran filtrate and 5% molasses. This culture was finally added in the fish-molasses mixture. Alpha-hydroxy acids were isolated from the fermentation products.

EXAMPLE 2

This test was carried out to test fermentation with *L. plantarum*.

In 6000 kg small Baltic herring was mixed 1050 kg molasses, 263 kg rye bran and 131 kg of 10% hydrochloric acid. The mixture was inoculated with 60 liters of *L. plantarum* inoculation solution. After vigorous mixing, the suspended matter was allowed to ferment in a fermenter of 10,000 liter volume for seven days, in which time the fermentation was concluded and the fermented mass had a pH 3.9. The pulped mass contained 14.6% raw protein, 4.5% digestible protein, 9.8% free amino acids and only 0.3% insoluble protein. The amounts of hydroxy acids in the pulped mass were:

| | |
|---|---|
| d,l-lactic acid | 32 mg/ml |
| d,1-2-hydroxy-3-methyl butyric acid | 10 mg/ml |
| d,1-2-hydroxy-4-methyl valeric acid | 6.0 mg/ml |

EXAMPLE 3

This test was carried out to further test fermentation with *L. plantarum*.

In 7500 kg fresh blood was mixed 1360 kg molasses. 300 kg rye bran, 230 liter of 10% hydrochloric acid and 560 liter *L. plantarum* inoculation solution. The fermentation was carried out in a 10,000 liter fermenter for 6 days. After fermentation, the pH of the pulped mass was 4.1. The relatively viscous pulped mass contained 23.6% protein, of which 9.2% was digestible protein and 5.4% free amino acids. The amounts of hydroxy acids in the pulped mass were:

| | |
|---|---|
| d,l-lactic acid | 21 mg/ml |
| d,1-2-hydroxy-3-methyl butyric acid | 18 mg/ml |
| d,1-2-hydroxy-4-methyl valeric acid | 4.5 mg/ml |

EXAMPLE 4

This test was carried out to still further test fermentation with *L. plantarum*.

In 7750 kg milled and steamed abattoir waste, which was unsorted but free from cattle rumens, was mixed 920 kg molasses, 370 kg rye bran and 180 liter of 10% hydrochloric acid. Water was added so much as to make the mixture mechanically agitatable, after which 780 liter *L. plantarum* inoculation solution was added. The pulped mass was allowed to ferment in a 10,000 liter fermenter for one week, at the end of which the pH of the pulped mass was 4.0. The product contained d,l-lactic acid, d,1-2-hydroxy-3-methyl butyric acid and d,1-2-hydroxy-4-methyl valeric acid in a total concentration of 48 mg/ml.

EXAMPLE 5

This example was carried out to test the effect of hydroxy acids on the growth of *Salmonella infantis* bacterium in vitro.

In this example, an investigation was carried out into the sensitivity of *Salmonella infantis* bacterium representing the genus Salmonella to two hydroxy acids: L-2-hydroxy-3-methyl butyric acid (HMB) and L-2-hydroxy-4-methyl valeric acid (HMV). The acids were added to the MRS growth medium of the bacterium so that resulting concentrations were controlled to 0.03, 0.1 and 0.3%. The organism growth was followed at 37° C. for 20 hours by measuring the turbidity of the culture at 600 nm wavelength.

Figure 1B:
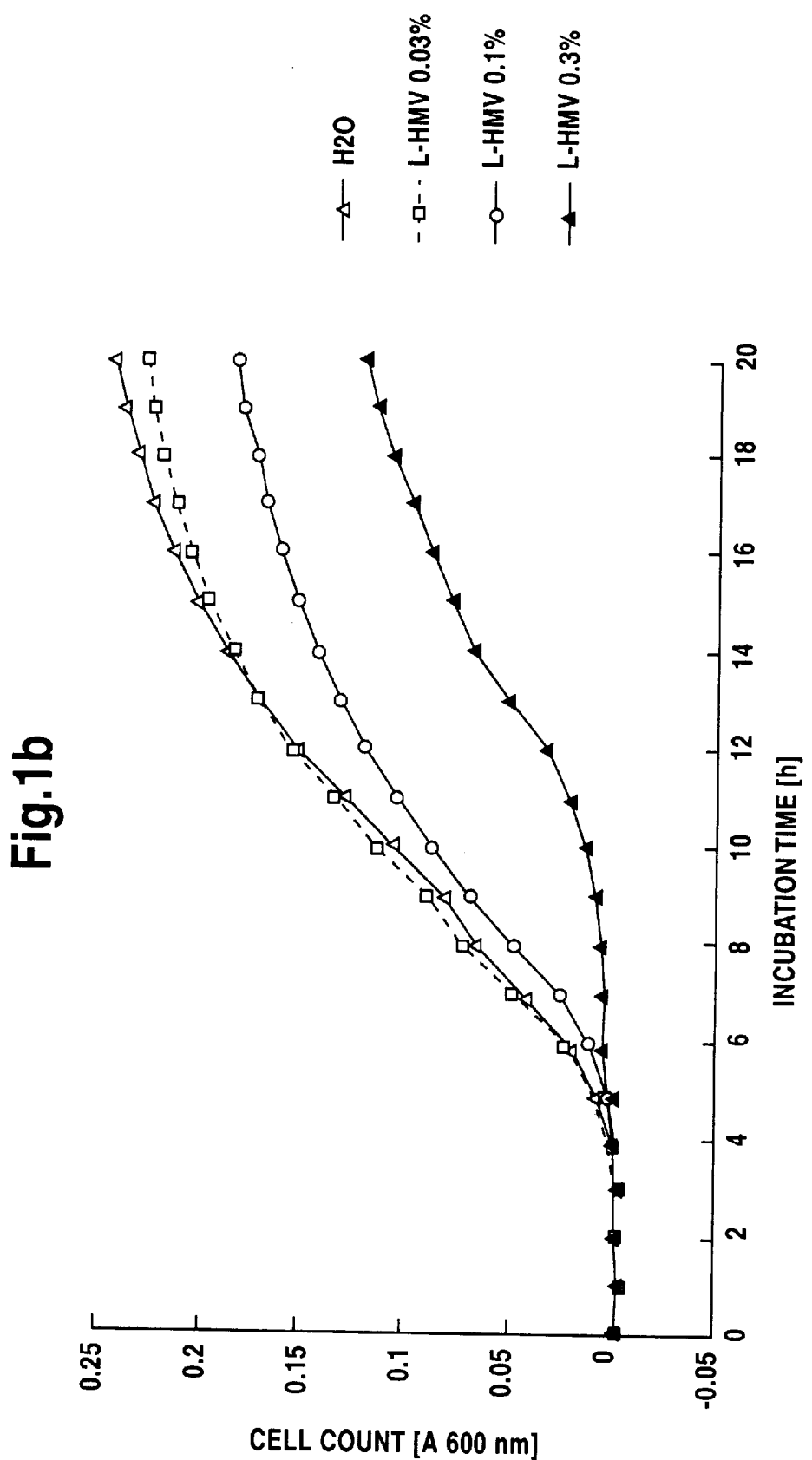

Referring to FIGS. 1a and 1b, the results shown therein indicated that both of the hydroxy acids tested in the example could inhibit the growth of the *Salmonella infantis* bacterium clearly at as low a level as 0.1% hydroxy acid concentration. HMV (FIG. 1b) was a slightly more effective inhibitor of bacterial growth than HMB (FIG. 1a). The results proved that both the hydroxy acids used in this example and other acids of comparable structure are feasible alternatives as Salmonella contaminations inhibiting additives in animal feeds.

EXAMPLE 6

This example was carried out to test the effect of hydroxy acids containing fish pulp on the viability of Salmonella bacteria in broiler population.

In the above Example 5, hydroxy acids were shown capable of inhibiting the growth of Salmonella bacteria under laboratory conditions at administration levels as low as 0.1% concentration. This example was carried out using fermented fish as the hydroxy acid source in an in vivo test using broilers as test animals. The fermented fish contained hydroxy acids HMB and HMV in a total concentration of about 2%. Such fish pulp was mixed by 10% in the base feed, whereby the final concentration of hydroxy acids in feed became 0.2%. This specially prepared feed was administered to poultry contaminated by *Salmonella oranienburg* bacteria. Of the 30,000 young chickens contaminated by *Salmonella oranienburg* in the poultryhouse, 10,000 were slaughtered. The remaining 20,000 chickens were fed for 10 days by feed prepared by *L. plantarum* fermentation from small fish and fish cleaning waste. After 10 days, the excretions of the chickens were free from *Salmonella oranienburg*. Equally, in autopsy the intestines of the chickens were found free from this microbe.

EXAMPLE 7

This test was carried out to test the efficacy of hydroxy acids in the eradication of Salmonella and Mycobacterium infections.

Chickens are well known to be susceptible to Salmonella infections. Although a fermentation product cannot be secondary post-infected with Salmonella species, it does not necessarily imply that a product intended for use as feed could not be harmful under in vivo conditions.

To test this possibility, 30 chickens of at the age of one day were intentionally inoculated with Salmonella by introducing 0.1 ml of a growing Salmonella culture into the alimentary tract of these chickens. A fermentation product processed with *L. plantarum* from fish and fish cleaning waste was mixed with drinking water which was freely available to the chickens. The chickens continuously were kept under maximally unhygienic conditions. During the test, the chickens were sequentially decapitated at constant intervals during one month and their alimentary tracts with other intestines were subjected in autopsy to bacteriological examinations. None of the examined intestines revealed a Salmonella infection.

A control test was performed by injecting a dose of a *Mycobacterium avium* culture into the *Musculus pectoralis* muscle of chickens. Resultingly, all chickens injected died during a short time. By contrast, when 0.2 ml of sterile filtered fermentation solution made from fish was injected 5 minutes prior to the bacterial contamination into the chickens' pectoral muscle, the subsequent injection of the tuberculotic bacterium culture caused no increase in the mortality of the chickens whatsoever. The only detectable effect was calcification of the muscle at the injection point. In pathological/anatomical and bacteriological examinations, these prophylactically treated chickens were entirely negative.

EXAMPLE 8

This test was carried out to test the effect of hydroxy acids on the growth of microbes isolated from the alimentary tract of broiler chickens in vitro.

In the example, the sensitivity of microbes isolated from the small intestine of broiler chickens to hydroxy acids were measured under laboratory conditions. For the test, a representative test organism species from each of the bacterium groups mentioned above was chosen. Of the hydroxy acids, HMB (2-hydroxy-3-methyl butric acid) and HMV (2-hydroxy-4-methyl valeric acid) were separately tested using their a mixture of their L- and D-forms as well as the pure L-form. The acids were added to the MRS growth medium of the bacterium so that resulting concentrations were controlled to 0.03, 0.1 and 0.3%. The organism growth was followed at 37° C. by measuring the turbidity of the culture at 600 nm wavelength.

Figure 2A:
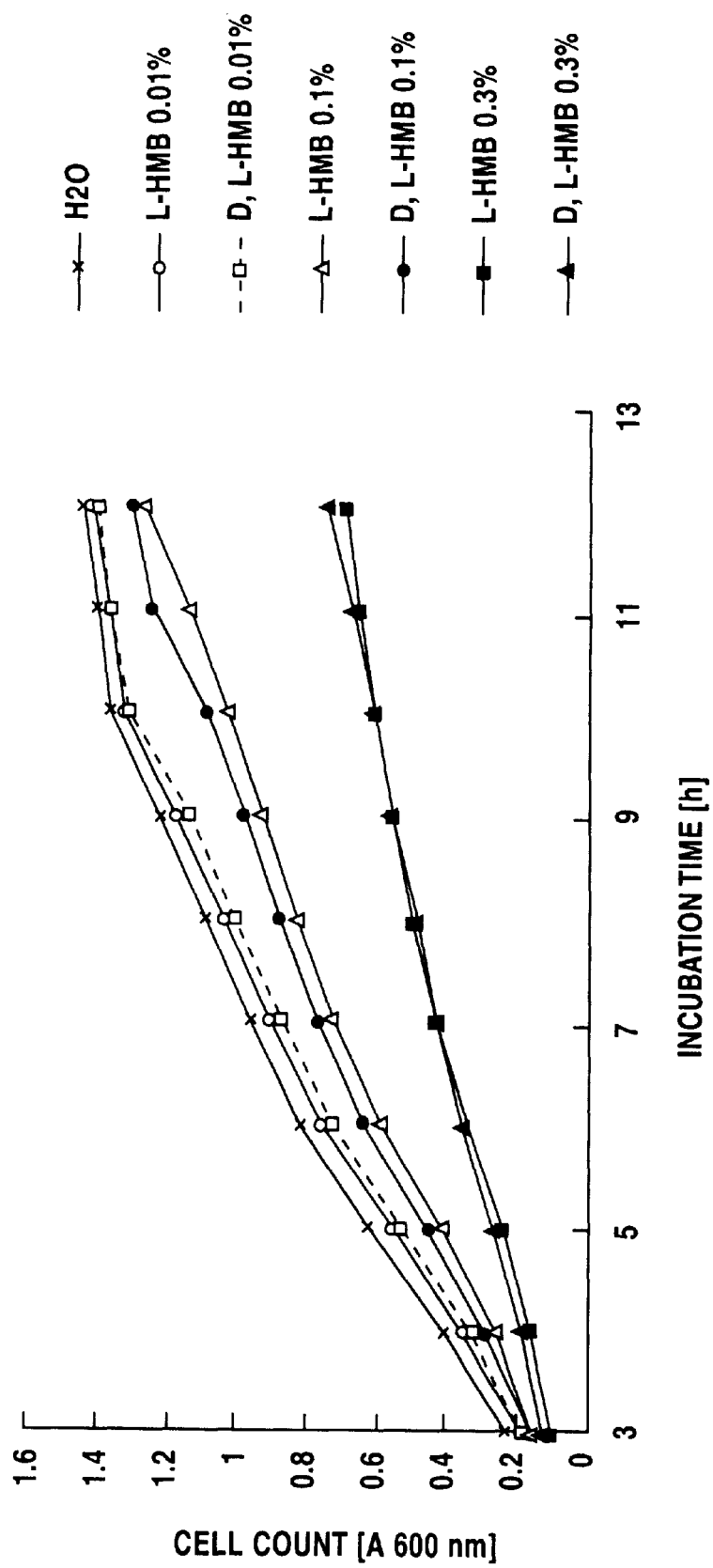
FIGS. 2*a* and 2*b* are plots of the efficacy of HMV and HMB, respectively, in inhibiting the growth of a coliform bacterium strain (104) isolated from the broiler chicken gastrointestinal tract.
Figure 2B:
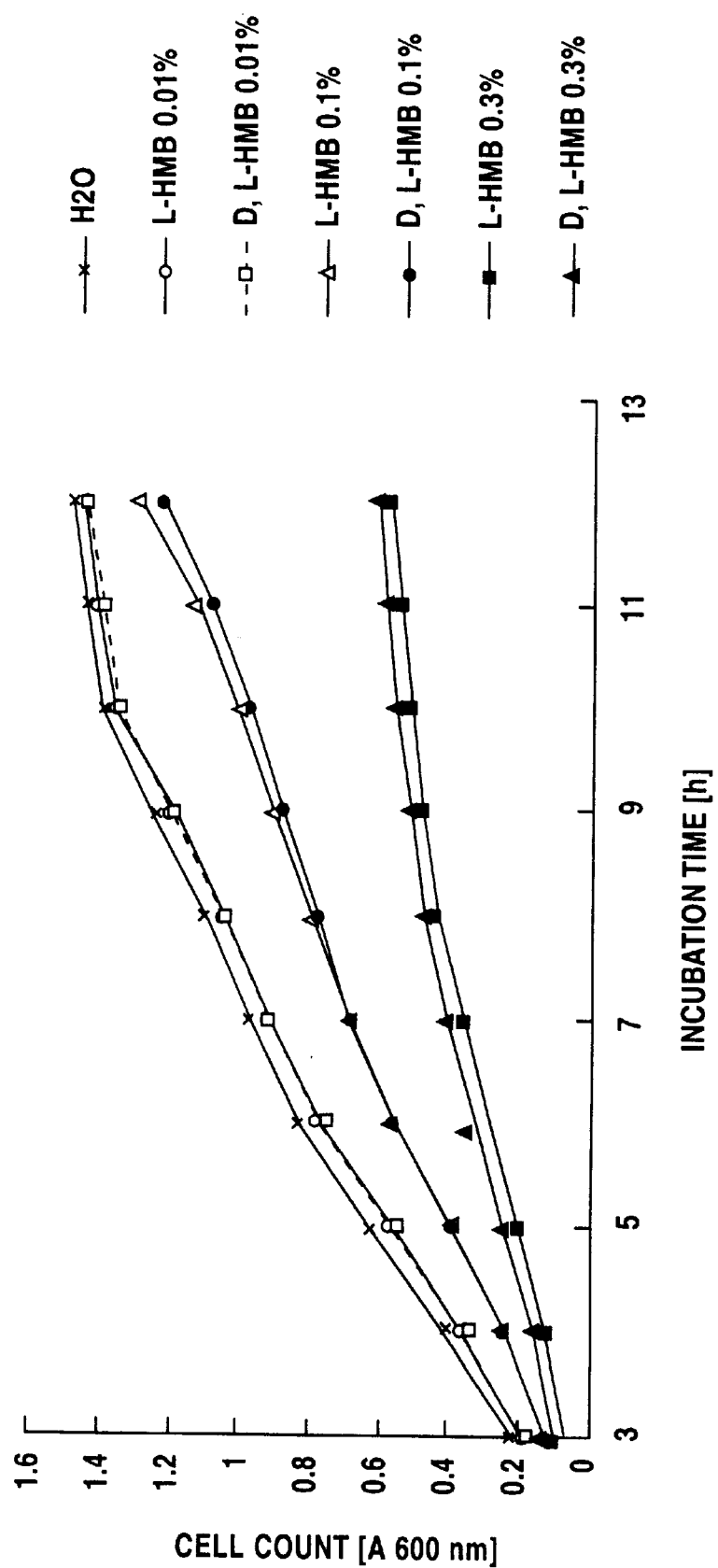
Figure 3A:
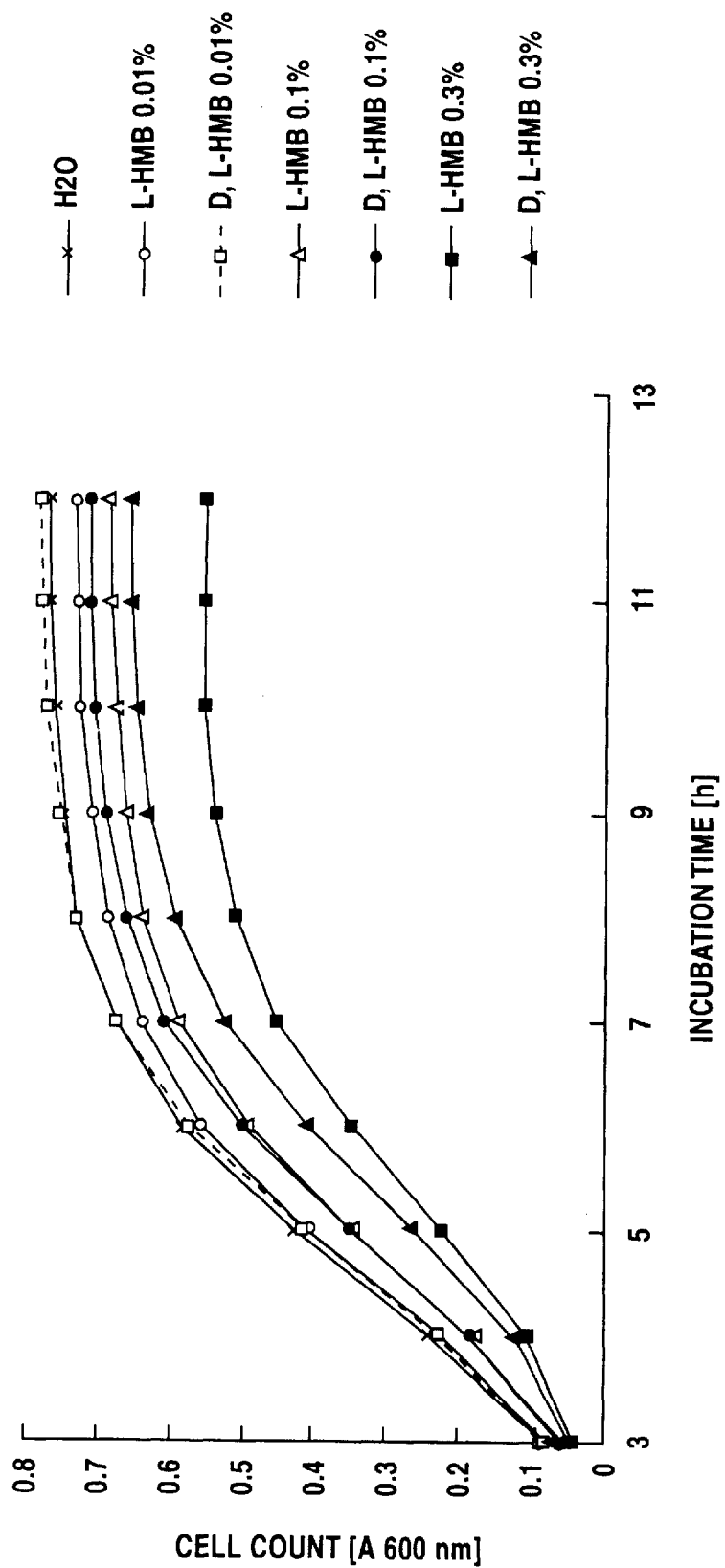

Referring to FIGS. 2a and 2b, the results shown therein indicated that the hydroxy acids tested in the example could effectively inhibit the growth of a coliform bacterium strain (104) isolated from the broiler chicken gastrointestinal tract already at as low as 0.1% hydroxy acid concentration. HMV was a slightly more effective inhibitor of bacterial growth than HMB. By contrast, the chirality of the acids did not modify the growth-inhibiting effect of the acids. FIGS. 3a and 3b portray the corresponding effect of the acids on the growth of the Enterococcus strain (111). Again a clear growth-inhibiting effect was found so that HVM was again more potent than HMB. Here, the chiral form of the acids seemed to modify the growth inhibiting efficacy so that the L-form was more effective. On the growth of a lactic bacterium strain (120), the tested hydroxy acids had an appreciably weaker inhibiting effect as compared to that detected on the growth of the coliform and enterococci bacteria. Only when the concentration was elevated to the highest level of 0.3%, a slight growth-inhibiting effect was noticed (FIGS. 4a and 4b). By contrast, neither the length of the carbon chain nor the chirality of the acids did modify their growth-inhibiting effect on lactic acid bacteria. The results provided that both the hydroxy acids used in this example and other acids of comparable structure can enhance the productivity of animals by reducing the competition of intestinal flora on the available nutrients. However, a much lower inhibiting effect on lactic acid bacteria was found. Accordingly, the acids used as additives in animal feeds can plausibly exert a beneficial effect on the state of the alimentary tract and health of the animal.

EXAMPLE 9

This test was carried out to test the effect of hydroxy acids on the growth of broiler chickens.

Example 8 above proved that the hydroxy acids (HMB and HMV) tested may have an effect on the amount and composition of microbial flora in the gastro-intestinal tract. It is also plausible that said acids may have additional, direct effects on the tissues of the host animal. The examination of such a total beneficial effect was performed in this in vivo test using a number of test animals.

Pure, chemically synthesized grades of the hydroxy acids (L-2-hydroxy-3-methyl butyric acid and L-2-hydroxy-4-methyl valeric acid) were mixed in the ratio 1:1 and then added in the feed of broilers using addition levels of 0, 200, 400, 600, 800 and 1000 gram per ton of feed. The differently prepared feeds were administered to broiler chicken test animal groups for 3 weeks, after which the test animals were weighed and the efficiency of feed utilization was computed.

Table 1 and FIG. 5 below the average weight of broilers in the different test animal groups after three weeks feeding. Hydroxy acids used in the test had a statistically significant growth-enhancing effect up to an addition level of 800 g/tn feed. The highest addition level (1000 g/tn feed) proved excessive, reducing the growth rate of the broilers as compared to the control feed.

Table 2 and FIG. 6 show the effect of the hydroxy acids on the efficiency of feed utilization in the different test animal groups after three weeks feeding. As the addition of hydroxy acids was increased, feed utilization was enhanced in a statistically significant manner up to the addition level of 800 g/tn feed.

TABLE 1

Effect of hydroxy acids on the growth of broilers

| Addition level of hydroxy acids [g/tn feed] | Average weight [g] | Standard error of mean [g] | p-value |
|---|---|---|---|
| 0 | 552 | 15 | 1.000 |
| 200 | 583 | 19 | 0.210 |
| 400 | 593 | 15 | 0.070 |
| 600 | 580 | 16 | 0.220 |
| 800 | 629 | 18 | 0.003 |
| 1000 | 531 | 13 | 0.290 |

TABLE 2

Effect of hydroxy acids on the efficiency of feed utilization

| Addition level of hydroxy acids [g/tn feed] | Feed utilization efficiency [g/g] | Standard error of mean [g/g] | p-value |
|---|---|---|---|
| 0 | 1.67 | 0.006 | 1.000 |
| 200 | 1.64 | 0.007 | 0.260 |
| 400 | 1.63 | 0.007 | 0.190 |
| 600 | 1.62 | 0.007 | 0.090 |
| 800 | 1.62 | 0.005 | 0.039 |
| 1000 | 1.68 | 0.009 | 0.860 |

EXAMPLE 10

This example was carried out to test the prophylactic efficacy of hydroxy acids against leucosis.

As known, leucosis is one of the most important poultry diseases in the Nordic countries. To examine the effect of the fermentation product of L. plantarum on poultry leucosis, 12 hens suffering from ocular leucosis were divided into two groups of 6 hens. The test was started on the 1st of April and continued to the 31st of December. During this time, the second group of 6 hens was fed with a feed complemented with the fermentation product added by 6 g per day, while the control group was fed with conventional feed. During the test, 1 hen in the test group died accidentally, while 3 of the control group hens died in leucosis. In the group fed with feed complemented with the fermentation product, the total production during the 9-month test was 965 pcs. eggs, while the control group fed with conventional feed produced only 581 pcs. eggs total. Expressed as average production per hen during 9 months, these figures correspond to 120 pcs. eggs in the group receiving the fermentation production and 72.6 pcs. eggs in the control group.

EXAMPLE 11

This example was carried out to examine the effect of fish/blood pulp made by fermentation on the egg production rate of hens.

For the example, three groups of hens were formed, each comprising 30 test animals. Complementing the normal protein in the base feed, the hens of group 1 received 8 g of fermented fish pulp per day, the hens of group 2 received 8 g of fermented blood product per day and the hens of group 3 received a corresponding amount of additional protein in the form of fish meal. Production per hen was 312 pcs. eggs in the group receiving fermented fish pulp. 290 pcs. eggs in the group receiving fermented blood product and 243 pcs. eggs in the group receiving the additional protein as fish meal. The fertilization percentage in the fish pulp receiving group was 100% and the hatch percentage of the offsprings was 86.7%. The corresponding figures in the blood product receiving group were 93.3% and 80%, while the fish meal receiving group remained at 90% and 68.3%, respectively. Blood hemoglobin concentrations in the siblings of both the fermented fish and blood product receiving groups were higher than in the control group receiving the fish meal.

Another feed test was performed using four groups of 38 hens each, of which group 1 received daily 8 g of fermented fish pulp per hen, group 2 received daily 8 g of fermented blood product per hen and the two other groups of 38 hens were used as control groups. During the 300-day test was, the fish pulp receiving group produced 7880 eggs, while its control group produced 7134 eggs. The blood product receiving group produced 8438 eggs, while its control group produced 7992 eggs. The fertility percentage in the fish pulp receiving group was 97.7% with a hatch percentage of 91.5% versus 93.8% and 85.4%, respectively, in the group receiving the blood product. In the control groups, the figures were on the average 93.8% and 86.2%, respectively.

According to a fat analysis performed, the amount of linoleic acid in the fat of eggs produced by the hens received fermented fish pulp was 13.4% versus 12.0% in the eggs of the control group. The content of dodecahexenoic acid in the fat of eggs laid by hens receiving fermented fish pulp was 2.7%, while only traces of this fatty acid could be found in the eggs of the control group. By contrast, the content of oleic acid in the eggs of the control group was higher at 43.5% versus 39.6% in the eggs of the fish meal receiving group. Hence, to some extent, accumulation of essential unsaturated fatty acids seems to occur in the fat of eggs laid by hens receiving fermented fish pulp.

EXAMPLE 12

This example was carried out in order to examine the effect of the *L. plantarum* fermentation product on the development of the Clostridium flora.

Feeding of pigs with an extremely high-protein feed causes after some time a strong growth of Clostridium flora in the intestinal tract of the pigs. For the example, three test were performed.

Test I. Two pigs forming a control group receiving low-protein feed and having their excreta almost free from *Clostridium perfringens* were administered daily 0.5 kg of said fermentation product for seven weeks. The titers of coliform and Enteroccus in the faeces of the pigs were lowered by one to two orders of magnitude.

Test II. Another group of two pigs were fed with fish meal enriched feed (14% fish meal). During this period, the pigs had developed a strong flora of *Clostridium perfringens* and a partial parakeratosis. Next, the fish meal in the feed was replaced by a *L. plantarum* fermentation product which was administered to the pigs daily 0.5 kg per pig. The protein content of the feed was kept approximately the same as when feeding with the fish flower containing feed. The titers of coliform and Enterococcus bacteria were decreased by one to two orders of magnitude in both pigs. A significant effect was that the *Clostridium perfringens* flora was decreased drastically. In both pigs, the bacterial count of this species was dropped from about 1 million/g excreta to zero.

Test III. A third group of pigs was fed with similar high-protein feed as the pigs of group II above. Also these pigs had a strongly developed *Clostridium perfringens* flora. These test animals had received in the feed a special addition, which had prevented the onset of parakeratosis. When the pigs were daily administered 0.5 kg of the fermentation product per pig, also in these pigs the *Clostridium perfringens* count was reduced from 1 million/g excreta to a few bacteria per gram. Also the titers of coliform and Enterococcus bacteria were decreased somewhat.

EXAMPLE 13

This example was carried out in order to examine the effect of the *L. plantarum* fermentation product on the blood hemoglobin, cholesterol, protein and calcium concentrations of sows and their offspring pigs as well as the oleic acid content of their fat.

For the test, five sows were fed with the *L. plantarum* fermentation product, while five other sows were fed with whey and buttermilk, respectively. Blood samples were taken from the sows from 7 to 2 days ante partum and from 1 to 6 and 14 days post partum. From the pigs the blood samples were taken at the age of 4 days.

Mortality of the pigs in the control group was 23.5% versus 13.8% in the group receiving the fermentation product.

The hemoglobin, total protein and calcium concentrations of blood were of the same order of magnitude in both groups of sows. By contrast, the hemoglobin concentrations in the blood of pigs borne by sows receiving the fermentation product were higher (8.9%, with a variation range of 8.4–11.4%) than the concentrations (7.0%, with a variation range of 6.4–10.2%) in the pigs borne by sows fed with whey and buttermilk. The proportion of gammaglobulin in the blood proteins was higher in the group fed with the fermentation product than in the control group.

When the offspring pigs borne by sows fed with the fermentation product were administered the same fermentation product up to their slaughtering, it turned out that these pigs had a lower blood cholesterol level than the pigs of the control group (117.5 mg % versus 156.5 mg % in the control group). The total linoleic and linolenic acid content in the lard of the pigs fed with the fermentation product was 13.7–14.3% versus 10.3–11.0% in the control group. The proportion of oleic acid was correspondingly higher in the control group than in the group fed with the fermentation product. The iodine number in the latter group was 66.9 versus 58.0 in the control group.

The storage properties of the flesh obtained from pigs fed with the fermentation product was slightly inferior to that of the control group animals. However, their fat became rancid at an unconventionally slow rate. Flesh consistency between the groups did not differ essentially, which is an unexpected result as flesh consistency is normally related to the iodine number. Yet, the difference between the iodine numbers of the group fed with the fermentation product and the control group fed with whey, namely, 66.9 versus 58.0, was statistically significant.

EXAMPLE 14

This example was carried out to examine the effect of the *L. plantarum* fermentation product on the growth rate of pigs.

The test group of 49 pigs in this example had an average weight of 28.0 kg per pig. Feeding was arranged as dry feed administered from an automat. Water supply was unlimited and continuous. The feed mixture was conventional. As is shown in the table below, the average weight had by January 19 reached 52.0 kg, except for four growth-retarded pigs having an average weight as low as 34.3 kg. These four pigs were placed in a separate cage and separately administered a daily dose of 0.2 liter per pig of a fermentation product made with *L. plantarum*. In the table below, the weight development of these four pigs is listed as Group B, while Group A is formed by the other 45 pigs.

| | Group A | | Group B | |
|---|---|---|---|---|
| Date | Average weight [kg] | | Average weight [kg] | |
| 19.01 | 52.0 | | 34.3 | |
| 26.01 | 56.0 | | 39.1 | |
| 02.02 | 58.0 | | 43.4 | |
| 09.02 | 62.0 | | 48.0 | |
| 16.02 | 65.0 | | 51.8 | |
| 23.02 | 72.0 | | 54.2 | |
| 02.03 | 76.0 | | 58.5 | |
| 06.03 | 76.0 | 41 pcs. | — | |
| 09.03 | 80.0 | | 63.0 | |
| 13.03 | 80.0 | 39 pcs. | — | |
| 16.03 | 85.0 | 30 pcs. | 66.0 | |
| 23.03 | 85.0 | 19 pcs. | 70.5 | |
| 30.03 | 85.0 | 11 pcs. | 80.0 | 3 pcs. |
| 06.04 | 85.0 | 7 pcs. | 85.0 | 1 pc. |
| 13.04 | 85.0 | 1 pc. | 85.0 | 1 pc. |

It will be noted that the initially growth-retarded pigs reached their normal slaughtering weight of 80–90 kg in almost the same time as the control animals in Group A. Also noteworthy is that the incremental feed consumption in Group B at 3.42 feed units per 1 kg additional weight is essentially lower than the corresponding figure of 4.38 feed units per 1 kg additional weight in Group A.

To those versed in the art, it is obvious that the different embodiments of the invention are not limited to those described above, but rather, can be varied within the scope and spirit disclosed in the annexed claims.

What is claimed is:

1. A method for promoting animal growth and improving feed utilization efficiency by an animal, comprising adding to animal feed at least one branched hydroxy acid which has four to six carbon atoms, and one substituent which is a hydroxy group in the α-position, at a rate of 200–800 mg per 1000 kg of animal feed, and feeding said animal feed to the animal.

2. A method as in claim 1, wherein the hydroxy acid is selected from the group consisting of 2-hydroxy-3-methyl butyric acid and 2-hydroxy-4-methyl valeric acid.

3. A method as in claim 1, wherein the hydroxy acid is selected from the group consisting of chemically synthesized hydroxy acids and biochemically produced hydroxy acids.

4. A method as in claim 1, wherein the daily administration rate of the hydroxy acid is not greater than 500 mg of hydroxy acid per lightweight kg.

5. A method as in claim 4, wherein the hydroxy acid is administered to the animal at a daily administration rate of 20–100 mg of hydroxy acid per lightweight kg.

6. A composition comprising:
   (1) an animal feed; and
   (2) at least one branched hydroxy acid which has four to six carbon atoms, and one substituent which is a hydroxy group in the α-position, wherein the amount of hydroxy acid is 200–800 g per 1000 kg of animal feed.

7. A method as in claim 6, wherein the hydroxy acid is selected from the group consisting of 2-hydroxy-3-methyl butyric acid and 2-hydroxy-4-methyl valeric acid.

8. A composition as in claim 6, wherein the hydroxy acid is selected from the group consisting of chemically synthesized hydroxy acids and biochemically produced hydroxy acids.

9. A method of producing an improved animal feed, comprising the step of adding to an animal feed at least one branched hydroxy acid which has four to six carbon atoms, and one substituent which is a hydroxy group in the α-position, at a rate of 200–800 g per 1000 kg of animal feed.

10. A method as in claim 9, wherein the hydroxy acid is selected from the group consisting of 2-hydroxy-3-methyl butyric acid and 2-hydroxy-4-methyl valeric acid.

11. A method as in claim 9, wherein the hydroxy acid is selected from the group consisting of chemically synthesized hydroxy acids and biochemically produced hydroxy acids.

\* \* \* \* \*